United States Patent [19]

Grossman et al.

[11] Patent Number: 5,056,359
[45] Date of Patent: Oct. 15, 1991

[54] METHOD AND APPARATUS TO MEASURE VAPOR PRESSURE IN A FLOW SYSTEM

[75] Inventors: Mark W. Grossman, Belmont; Oscar Biblarz, Swampscott, both of Mass.

[73] Assignee: GTE Products Corporation, Danvers, Mass.

[21] Appl. No.: 323,640

[22] Filed: Mar. 15, 1989

[51] Int. Cl.⁵ ............................................... G01N 7/00
[52] U.S. Cl. .................................. 73/64.2; 204/157.21
[58] Field of Search ................................ 73/64.2, 29; 204/157.21

[56] References Cited

U.S. PATENT DOCUMENTS

| | | | |
|---|---|---|---|
| 3,379,252 | 4/1983 | Work | 313/485 |
| 3,897,331 | 7/1975 | Smith | 209/10 |
| 3,983,019 | 9/1976 | Botter nee Bergheaud | 204/157 R |
| 4,514,363 | 4/1985 | Durbin | 423/3 |
| 4,527,086 | 7/1985 | Maya | 313/485 |
| 4,648,951 | 3/1987 | Maya | 204/157.21 |
| 4,678,550 | 7/1987 | Grossman et al. | 204/105 R |
| 4,713,547 | 12/1987 | Grossman | 250/373 |

FOREIGN PATENT DOCUMENTS 0280788 12/1987 European Pat. Off. .
0281687 12/1987 European Pat. Off. .

OTHER PUBLICATIONS

Webster and Zare, J. Phys. Chem., 85:1302 (1981).
McDowell et al., Can. J. Chem., 37: 1432 (1959).
Gunning and Swartz, Adv. Photochem., 1:209 (1963).
Weymouth, Electric Discharge Lamps, MIT Press 1971.
Grossman et al., U.S. Ser. No. 815,150, filed Dec. 31, 1985.
Maya et al., Science, 226:435–436, (1984).
R. E. Trebal, "Mass-Transfer Operations" McGraw-Hill Book Company.
F. Gucker, Jr. and R. H. Munch, J. Amer. Chem. soc., 59:1275 (1937).
Nesmeyanov, Vapor Pressure of the Elements, Academic Press, New York (1963).

Primary Examiner—Hezron E. Williams
Assistant Examiner—Joseph W. Roskos
Attorney, Agent, or Firm—Ernest V. Linek

[57] ABSTRACT

The present invention is directed to a method for determining, by a condensation method, the vapor pressure of a material with a known vapor pressure versus temperature characteristic, in a flow system particularly in a mercury isotope enrichment process.

4 Claims, 1 Drawing Sheet

METHOD AND APPARATUS TO MEASURE VAPOR PRESSURE IN A FLOW SYSTEM

STATEMENT OF GOVERNMENT INTEREST

The Government of the United States of America has rights in this invention pursuant to Subcontract 4540710 under Prime Contract DE-AC03-76SF00098 awarded by the Department of Energy.

FIELD OF THE INVENTION

The present invention is directed to a method and apparatus useful in the isotopic enrichment of a predetermined isotope of mercury (Hg) from a naturally occurring mercury mixture While the present invention may be used in the enrichment of any one of the seven naturally occurring isotopes of mercury ($^{202}$Hg, $^{200}$Hg, $^{199}$Hg, $^{201}$Hg, $^{198}$Hg, $^{204}$Hg, and $^{196}$Hg,) it has particularly advantageous application in the photochemical enrichment of the $^{196}$Hg isotope, which has a natural abundance of only about 0.146 percent.

Photochemical mercury enrichment processes are well known and have been well documented in the literature. See for example, Webster and Zare, *J. Phys. Chem.*, 85: 1302 (1981); McDowell et al., *Can. J. Chem.*, 37: 1432 (1959); Gunning and Swartz, *Adv. Photochem.*, 1: 209 (1963) and U.S. Pat. Nos., 4,678,550, 4,648,951, and 4,514,363, the teachings of which are hereby incorporated herein by reference.

BACKGROUND OF THE INVENTION

Many devices utilize mercury in their operation, particularly in the field of electric lamps and lighting. Such devices include arc discharge lamps which typically employ mercury as one of the vaporizable components therein. See, for example, Waymouth, *Electric Discharge Lamps*, MIT Press 1971 for a description of the basic principles of such lamps.

In U.S. Pat. No. 4,379,252, (the '252 patent), the advantages of utilizing higher than normal levels of $^{196}$Hg in the Hg added to fluorescent lamps are described and include unexpectedly high efficiency gains in light output. The disclosure of this patent is hereby incorporated herein by reference.

The drawback of using this isotope lies in its high cost. For example, using conventional enrichment techniques, mercury which has been enhanced to contain about 35% of the $^{196}$Hg isotope can cost about $500 per milligram While only sub-milligram quantities of this isotope need be added to an incandescent lamp to afford beneficial results, economic realities always play a part in consumer products. Accordingly, it is easy to understand why more economical methods of obtaining this isotope continue to be sought.

Isotopically enriched mercury can be produced by a number of methods. One method involves photosensitized chemical reactions utilizing elemental mercury and various compounds The compounds HCl and $O_2$ react with mercury atoms when the mercury atoms are excited by resonance radiation, in particular, 2537Å radiation produced in a Hg ($^3$P - $^1$S$_o$) transition generating isotopically selective reactions Thus, the Hg compound formed contains Hg enriched in a particular isotope, and the Hg must be separated from the compound into its liquid or free state (i.e., elemental Hg)) in order to recover the isotopically enriched metal.

INFORMATION DISCLOSURE

The following documents are recited as general background information with respect to the subject matter of the present invention. To the extent deemed necessary by artisans of ordinary skill in the art to which this invention pertains, the teachings of these documents are hereby incorporated herein by reference.

Grossman, U.S. Pat. No. 4,713,547;
Grossman et al., U.S. Pat. No. 4,678,550;
Maya, U.S. Pat. No. 4,527,086;
Durbin, U.S. Pat. No. 4,514,363;
Work et al., U.S. Pat. No. 3,379,252;
Botter nee Bergheaud et al., U.S. Pat. No. 3,983,019;
Smith et al., U.S. Pat. No. 3,897,331;
Grossman et al., U.S.S.N. 815,150, filed 31 December 1985, now U.S. Pat. No. 4,776,932;
European Patent Publication No. 0 281 687, published 14 September 1988, claiming priority of U.S.S.N 947,217, filed 29 December 1986;
European Patent Publication No. 0 280 788, published 7 September 1988, claiming priority of U.S.S.N. 947,216, filed 29 December 1986, now U.S. Pat. No. 4,800;
R. E. Treybal, "Mass-Transfer Operations," McGraw-Hill Book Company; and
F. Gucker Jr. and R. H. Munch, *J. Amer. Chem. Soc*, 59: 1275 (1937).

SUMMARY OF THE INVENTION

The vapor pressure of a material with a known vapor pressure versus temperature characteristic can be determined in a flow system by a condensation method. Alternatively if a condensable vapor is perfectly entrained by a non condensing gas whose flow velocity is known the vapor pressure of the condensable vapor can be determined in a batch mode.

These techniques have been used to verify that the carrier gas in a Hg-196 isotope separation process is fully saturated with mercury vapor and also to measure the vapor pressure of the product formed in the photochemical reactor.

DETAILED DESCRIPTION OF THE PREFERRED EMBODIMENTS

During operation of a photochemical Hg$^{196}$ reactor it is of interest to know the mercury density in the reaction zone. If the carrier gas is saturated in a region then the density in this region is given by the vapor-liquid equilibrium density determined by the temperature fixes the hg density. It is therefore of interest to know whether the carrier gas is saturated.

Additionally, in the case of formation of a product with a substantial vapor pressure it is of interest to be able to estimate this vapor pressure for the operating conditions being used. One especially preferred case involves a the use of a packed bed reactor, which is described in copending application Ser. No. 07/289,168, filed 23 December 1988, by M. W. Grossman and R. Speer. The disclosure of that application is hereby incorporated herein by reference.

Figure 1:
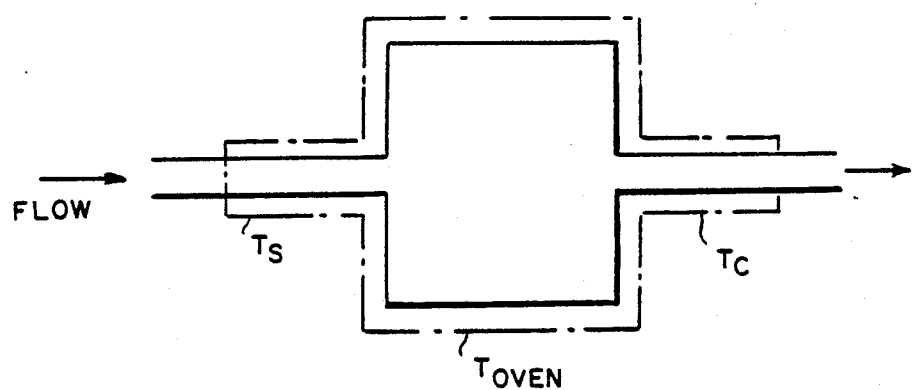
FIG. 1 shows a schematic of the device used to measure vapor pressure in a flow system.

FIG. 1 shows a schematic of the device used. Mercury is heated to a temperature of about $T_s = 80°$ C., the reactor temperature is $T_{oven} = 81°$ C. and $T_c$ is varied. At $T_c$ between 77° C. and 80° C. mercury is observed to condense on the wall of the tube carrying the gas mixture while at $T_c = 83°$ to 88; ° no condensation is observed In these cases mercury droplets are either observed to form or not on a quartz transfer tube. In this way the carrier gas was seen to be approximately saturated with mercury at vapor-pressure temperature of 77° C. to 80° C.

Under conditions in which the carrier gas molar flow rate and pressure or an entrained component's molar flow rate and pressure are known the vapor pressure of the product can be determined as set forth herein.

The following definitions are used herein in defining the apparatus and processing necessary to determine mercury vapor pressure in an isotope enrichment process:

| | |
|---|---|
| $T_s =$ | temperature of saturated Hg vapor in entrainment zone |
| $T_{oven} =$ | oven temperature |
| $T_c =$ | temperature of downstream collector |
| $Q =$ | mercury flow rate |
| $n =$ | mercury density |
| $vA =$ | volumetric flow rate |
| $Q_p =$ | product flow rate |
| $n =$ | mercury density |
| $vA =$ | volumetric flow rate |
| $Q_p =$ | product flow rate |
| $n_p =$ | product density |
| $P_p =$ | product pressure |
| $P =$ | $H_g$ pressure |

For plug flow conditions $$Q = n\, vA \qquad (1)$$

where equation (1) is a particle or molar relationship. For perfect entrainment $vA$ is the same for each component. Also for our operating conditions the ideal gas law is true.

Thus,
$$Q_p = n_p Q/n = P_p Q/p$$

For saturated conditions at $T_s = 73°$
$P = 59 mT$

The product yield is about 0.5 gm/hr, most of which is transported out of the reactor region at $T_{oven} = 76°$ C. Thus Qp is approximated by 0.5 gm/hr.

$$\text{Thus } P_p = \frac{Q_p}{Q} \cdot P$$

The above rate equation gives a $P_p = 0.9$ mT at 76° C. Using the data present in the reference of Gucker and Munch (supra) we found an empherical extrapolation to be:

$$\ln * P_p = 22.2 \frac{-1.0 \times 10^4}{T}$$

where $P_p$ is in Torr and T is in °K. This gives $P_p = 0.5$ mT which implies that our method will result in a good estimate of $P_p$.

In terms of molecular flow rates, the product vapor is assumed to be HgCl, the gram molecular weight of which (GMW) is 235:

Thus, $$P_p = (0.5/27.4)(200/235) * 59 = 0.9\ mT$$

Two improvements to this method are first, utilize $T_c$ to collect all product evaporated from the $T_{oven}$ region and then measure the mass of the collected product. Second, measuring Q, vA can be increased until no more product deposits in $T_{oven}$. The skilled artisan will recognize that these two modifications permit a more accurate measure of $P_p$.

For example, two experimental runs were made to determine the effectiveness of this method. Runs 1 and 2 were operated at similar conditions except the carrier gas flow velocity in run 2 was double that of run 1, which resulted in most of the product depositing outside of $T_{oven}$. For these cases $T_{oven} = 76°$ C., $Q_{HCl} = 200$ gm/hr (5.6 moles/hr) run 1 and $Q_{HCl} = 400$ gm/hr (11 moles/hr) run 2.

During run 1 the mercury flow rate was $Q = 13.7$ gm/hr (0.068 moles/hr). If the pressure and temperature just upstream of $T_{oven}$ in run 2 were identical to run 1 than in that run $Q = 27.4$ gm/hr (0.14 moles/hr).

All of the standard elements of the reactor system, i.e., the lamp, the filter, and the reactor vessel are formed of a material which is transparent to the desired excitation radiation, particularly 253.7 nm (2537 Å) for $^{196}Hg$. One preferred material is quartz. While the lamp used in the reactor of the present invention may be any low pressure (e.g., about 2.5 Torr) electric discharge type lamp which transmits radiation of about 253.7 nm, those using microwave cavities for the excitation are preferred.

An especially preferred lamp comprises an electroded mercury-inert gas lamp. At least two electrodes are positioned and sealed at each end of a sealed lamp envelope which contains mercury vapor and one or more inert gases. The sealed lamp envelope is surrounded at least in part by an elongated tube which defines a region for controlling a heat exchange medium which controls the temperature of the inner, sealed lamp envelope.

In one embodiment, uniform temperature is created in the Hg lamp by circulating $H_2O$ at a predetermined temperature about an isolated section of the lamp. Other fluids, or inert gases such as argon, helium, xenon and neon, can be selected depending on their boiling point behavior to provide the desired uniform temperature of the inner discharge envelope.

The circulating heat transfer medium also prevents the formation of $O_3$ (ozone) by purging $O_2$ in the vicinity of the lamp. Ozone is created when $O_2$ is exposed to 185 nm radiation which may be emitted by the lamp. Ozone, in turn, absorbs various wavelengths of radiation emitted from the lamp. This is undesirable because radiation having a wavelength of 253.7 nm, useful for the photochemical separation of $^{196}Hg$, is absorbed of $O_3$. Thus, in a preferred embodiment, a fluid or inert gas is circulated about the entire exterior of the lamp envelope, thereby purging all of the $O_2$ from the immediate vicinity of the envelope. This allows for a greater emission intensity of the particular, desired radiation from the lamp envelope.

In a preferred embodiment, the outer lamp jacket comprises a quartz cylinder. This outer jacket serves several purposes. First, it allows for the use of a gas purge, if desired, for eliminating $O_2$ about the transmission section, thereby reducing $O_3$ formation. Second, if the outer jacket is designed to be demountable, it permits the interchange of different inner lamp envelopes. This makes possible the isolation of different Hg isotopic distributions using the same outer jacket. Also, lamp envelopes having different diameters can be used to affect the emitted linewidth of radiation.

The fact that the outer tube can be demountable allows for the use of outer tubes of different types of materials which can selectively filter certain emitted wavelengths. For example, by changing the outer tube material to Vycor 7910, it is possible to filter wavelengths below 200 nm thereby eliminating ozone formation in the region surrounding the lamp.

Figure 2:
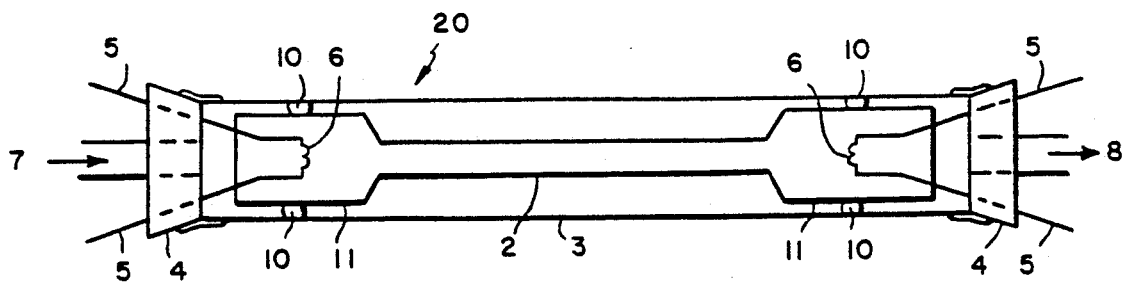
FIG. 2 illustrates one preferred monoisotopic lamp used in the process of the present invention.

FIG. 2 illustrates the preferred lamp which is used in the reactor of this invention.

The mercury lamp 20 of FIG. 2 comprises an inner lamp envelope 2 and an outer jacket 3. In the preferred embodiment, both the envelope 2 and the outer jacket are constructed of quartz. The envelope 2 can be of various diameters depending on the desired optical depth. A larger diameter provides greater power density and broader bandwidth. For the isotopic separation of $^{196}Hg$, the inner diameter of the envelope is typically about 10 nm. The envelope 2 typically contains a source of Hg such as elemental Hg as well as an inert gas such as argon. However, any inert gas which is compatible with Hg vapor can be used. Typically, between about 1 and 2 mg of Hg is contained within lamp envelopes which have an inner diameter of about 10 mm. The length of the lamp can be from about 30–150 cm with a preferred length of about 40 cm.

A tapered stopper 4, typically of an elastomeric material, is disposed at each distal end of the outer jacket 3 and serves to substantially center the outer jacket around at least one section of the envelope 2. Furthermore, the tapered stopper guides and positions an electrode lead 5 through both the stopper and the outer jacket, and into the envelope where it provides current for the electrodes 6. In the preferred embodiment, the electrodes are shaped as coils and able to withstand a current of at least about 5 amperes. The tapered stoppers also contain openings in their centers which provide for an inlet 7 and outlet 8 stream of circulating heat transfer medium which is preferably water. The heat transfer medium circulates about at least one portion of the inner discharge envelope 2. The heat transfer medium then exits the lamp at outlet 8 contained in the outer jacket. Tubes, 11, preferably comprising a heat resistant glass are connected to each end of the envelope to provide regions to contain the electrodes and to further provide regions for mounting the envelope within the jacket. These tubes 11 are preferably separated from the outer tube with spacers 10 preferably comprising elastomeric materials. It is pointed out that the spacers 11 must have openings which allow the heat transfer medium to travel through the lamp.

The temperature of the inner envelope 2 is controlled by the temperature of the circulating heat transfer medium. As the temperature of the heat transfer medium is increased or decreased, the corresponding temperature of the inner envelope also increases or decreases. The linewidth of the emitted radiation is typically affected greatly by temperatures between 15° C. and 50° C. The emission intensity depends strongly on the temperature of the inner envelope.

The entire lamp assembly can be placed within a mercury vapor filter. In one preferred embodiment, the filter comprises a hollow, axial elongated torus containing mercury vapor and an inert gas. This structure can be formed by the combination of two tubes, preferably quartz, where an inner tube is inserted into an outer tube and the tubes are sealed at both ends. This encloses a medium which can be made to contain a gaseous Hg vapor medium which transmits wavelengths of light desirable for the photochemical separation of $^{196}Hg$ or specific isotopes of Hg.

In a preferred embodiment of this invention $^{196}Hg$ is produced by enriching mercury compounds using radiation with a wavelength of 253.7 nm. The control of the specific wavelength is very dependent upon the vapor equilibrium temperature within the lamp envelope, which depends, in turn, upon the lowest temperature within the envelope. The vapor pressure of Hg within the envelope (for useful mercury isotope separation) and the intensity of the emitted radiation are proportional with a variation of about 10–15%.

If the intensity of radiation emitted from the lamp increases, the corresponding linewidth of the emitted radiation also increases. This causes other isotopes of mercury to become excited Such an effect is undesirable, as it leads to a separation which yields a product having lower isotopic specificity. Thus, it is important to control the vapor pressure of the lamps to ensure that radiation of the proper linewidth is emitted. For a further explanation of the relationship between lamp temperature, radiation intensity and linewidth of the radiation see Maya et al., *Science,* 226: 435–436 (1984), the teachings of which are incorporated herein by reference.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method for determining the vapor pressure of mercury in a photochemical mercury enrichment process ($^{196}Hg$) which comprises the steps of:
   (1) flowing enriched mercury vapor through a vapor pressure monitor having at least three independently controlled temperature regions or zones, (a) an entrainment zone, (b) an oven zone, and (c) a collector zone;
   (2) heating said vapor pressure monitor such that the mercury is heated to a first temperature ($T_s$) in the entrainment zone;
   (3) passing the heated mercury to the over zone heated to temperature ($T_{oven}$) and thereafter;
   (4) passing the mercury to the collector zone, wherein the temperature in the collector zone ($T_c$) is varied among predetermined temperatures;
   (5) monitoring the mercury flowing through the collector zone for condensation at the variable temperatures used for $T_c$; and
   (6) when condensation is detected, measuring the mercury flow rate Q, and solving the following equations for $P_p$, the product vapor pressure:

$$Q = n \, vA$$

(b) $$Q_p = n_p \frac{Q}{n} = P_p \frac{Q}{p}$$

-continued (c) $P_p = \dfrac{Q_p}{Q} \cdot P$ wherein:
Q = mercury flow rate
n = mercury density
vA = volumetric flow rate
$Q_p$ = product flow rate
$n_p$ = product density
$P_p$ = product pressure
P = Hg pressure.

2. The process of claim 1, which further comprises collecting product mercury evaporated from the oven region at temperature $T_{oven}$ and condensed in the collection zone at temperature $T_c$, and measuring the mass of mercury collected.

3. The process of claim 1, which further comprises increasing $V_a$ until no further mercury product is deposited in the collector zone at temperature $T_c$n, and thereafter measuring Q.

4. Apparatus useful for indirectly determining the vapor pressure of mercury in a photochemical mercury enrichment process, as determined by measuring the mercury flow rate through a defined system, the apparatus comprising a flow vessel having three defined regions, first an entrainment region at its inlet end, second, an oven member connected at one end thereof to the outlet of the entrainment region, and being connected to the third region, an outlet member having a collector member at the downstream end thereof, the apparatus having independently variable temperature control means for these three defined regions, providing the following variable temperature zones:

$T_s$ = temperature of saturated Hg vapor in the entrainment region
$T_{oven}$ = oven member temperature
$T_c$ = temperature of downstream collector said flow vessel further including means for measuring the flow rate Q, of the mercury vapor passing through.

* * * * *